United States Patent [19]

Goldstein

[11] Patent Number: 4,817,616
[45] Date of Patent: Apr. 4, 1989

[54] AUTO SWITCH BIPLANE PROSTATE PROBE

[75] Inventor: Albert Goldstein, Ann Arbor, Mich.

[73] Assignee: Wayne State University, Detroit, Mich.

[21] Appl. No.: 114,501

[22] Filed: Oct. 30, 1987

[51] Int. Cl.⁴ .................................................. A61B 10/00
[52] U.S. Cl. .................................... 128/662.06; 128/4
[58] Field of Search ............................. 128/660–663, 128/4–6

[56] References Cited

U.S. PATENT DOCUMENTS 4,756,313  7/1988  Terwilliger ..................... 128/660

FOREIGN PATENT DOCUMENTS 3141022  4/1983  Fed. Rep. of Germany ...... 128/660
2073418  10/1981  United Kingdom .............. 128/660

OTHER PUBLICATIONS

Fornage, B. et al, "Improved Probe for Ultrasound Endoscopic Echography", Europ. Pat. Appln. No. 0139574, publ. May 1985.

*Primary Examiner*—Francis Jaworski
*Attorney, Agent, or Firm*—Reising, Ethington, Barnard, Perry & Milton

[57] ABSTRACT

A biplane ultrasound probe (10) including an outer casing (12) having a longitudinal axis and an inner member (14) mounted within the outer casing (12). A pair of scanning transducers (16,18) are mounted on the inner member (14) for respectively ultrasound scanning different orthogonal planes (23,25) of an adjacent object (20). The assembly includes a shifting mechanism for shifting the inner member (14) axially within the outer casing (12) independently of the outer casing (12) to move either one of the scanning transducers (16,18) into a unitary scanning position. The shifting mechanism further includes an actuator for actuating the one of the scanning probes (16,18) shifted into the scanning position to scan the object (20).

15 Claims, 1 Drawing Sheet

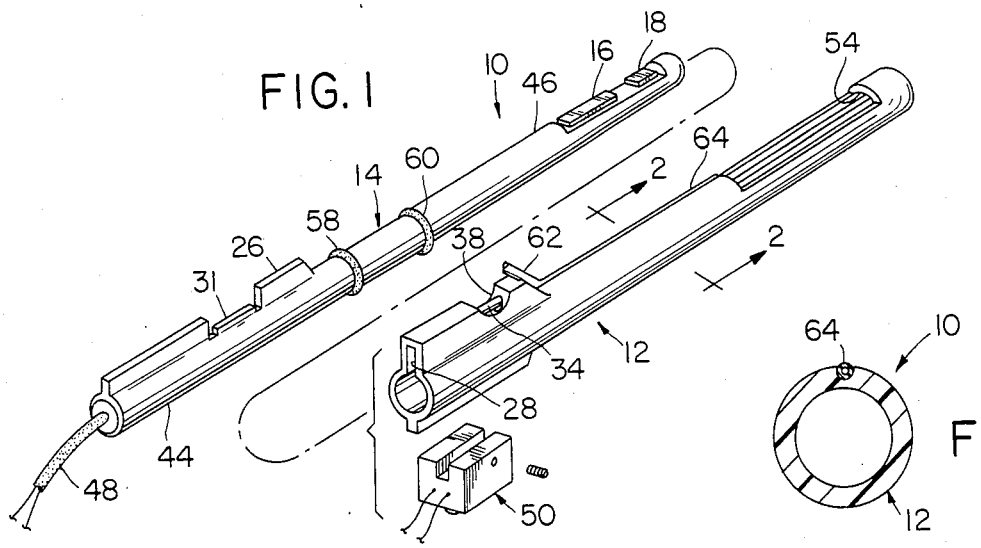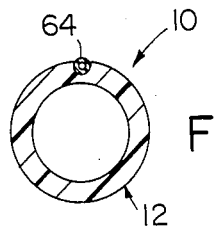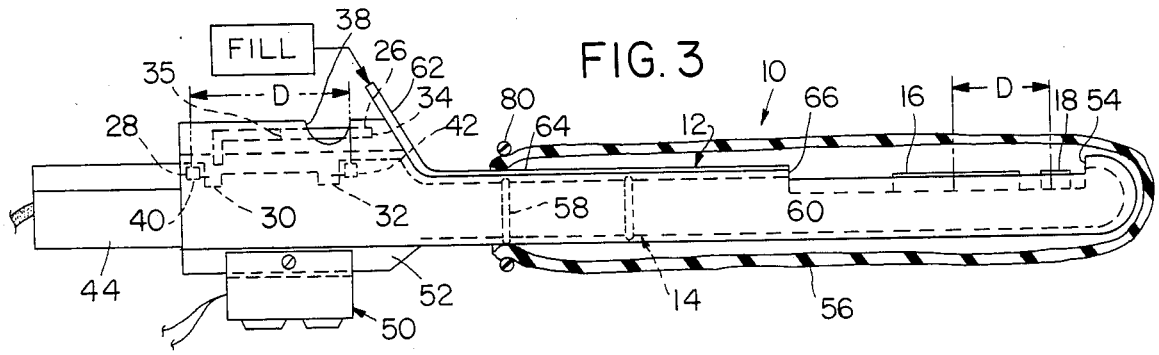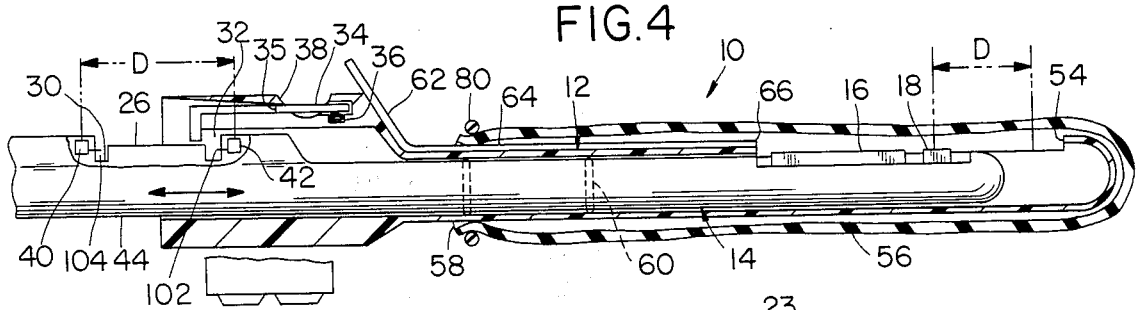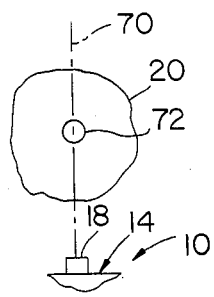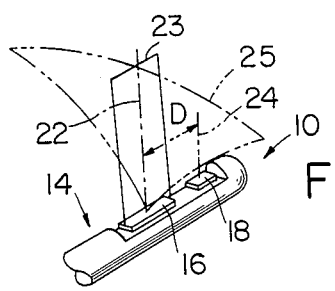

4,817,616

AUTO SWITCH BIPLANE PROSTATE PROBE

TECHNICAL FIELD

The present invention relates to ultrasound imaging equipment. More specifically, the present invention relates to ultrasound biplane probes.

BACKGROUND ART

Adenocarcinoma of the prostate gland is the second most common cancer in males over the age of 55. Lee et al "Transrectal Ultrasound in the Diagnosis of Prostate Cancer; Location, Echogenicity, Histopathology, and Staging", The Prostate 7:117-129 (1985). It has been shown that transrectal ultrasound can be used to detect cancer of the prostate gland as well as to demonstrate the extent of tumor involvement so as to enable accurate staging of the detected cancers. Id., Lee et al "Needle Aspiration and Core Biopsy of Prostate Cancer: Comparative Evaluation of Biplane or Transrectal US Guidance", Radiology 1987; 163:515520. Prostate endosonography has also been shown to be a potential screening test with the potential for improving the quality of life in patients affected by prostate carcinoma. A. Fleischer, "Prostatic Endosonography-a potential screening test", *Diagnostic Imaging*, page 78, 1987.

The aforementioned findings have been the result of the new use of ultrasound imaging and the acquisition of images of the prostate gland. These images are obtained by inserting a condom covered probe into the rectum and then inflating the condom with water. An ultrasound transducer mounted on the probe is then immediately adjacent to the small prostate gland and can transmit to and receive ultrasound signals from the prostate due to the water coupling. Because of this close proximity, high frequency, high quality, and small field of view images of the prostate can be obtained.

Recent efforts in this new imaging field have demonstrated that the small primary cancerous lesions that develop in the prostate's peripheral zone are clearly visible in the ultrasound images as hypoechoic regions. This means that not only is prostate cancer now visible for a study in all stages of development, but also that screening of the male population is possible.

The most recently developed equipment for ultrasound imaging is the biplane prostate probe. An example of such a prostate probe is the RT3600 Biplane Transrectal probe manufactured by General Electric Company, Medical Systems Group, Milwaukee, Wisconsin. Two ultrasound transducers are mounted on this probe. One is oriented to obtain a transaxial view of the prostate gland and the other is oriented to obtain a sagittal view. These two orthogonal views of the prostate have proved important in clinical imaging of the prostate and for ultrasound guided needle biopsies of the prostate. As stated in the aforementioned article by Lee et al in Radiology, experimental results suggest that transrectal ultrasound guidance of thin-needle biopsies is useful in diagnosing early prostate cancer.

With two transducers mounted in the biplane probe, the operator needs only to switch electrically between the two in order to change the plane of view. Previous to the development of the biplane probe, the operator was obliged to remove one probe from the patient's rectum and insert another before the operator could obtain a new view of the prostate. The biplane probe is more efficient to use and reduces the necessary examination time.

One important use of the biplane probe is the positive identification of suspected primary cancerous lesions in the peripheral zone of the prostate. Another important use is ultrasonically guiding the needle biopsy of lesions in order to accurately obtain a small tissue or cytology sample for pathological analysis. In both applications, it is essential for the operator to view the tissue area of interest in one scan plane and position it properly so that when the orthogonal scan plane is chosen, the area of interest is immediately viewed. This facility will permit the positive identification of a focal lesion in two orthogonal planes and will also permit the positive localization of the tip of the biopsy lesion using two orthogonal scan planes. The selection of the scan plane must also be made quickly and conveniently so that the operator does not move the probe in the patient's rectum during the switching procedure.

Most newly developed biplane probes consist of two transducers. One transducer is a linear array or phased array for sagittal imaging and the other is a phased array (or mechanical sector scanner) for transaxial imaging. These two transducers must be physically separated when mounted on the biplane probe. Usually, the transaxial transducer is mounted close to the tip of the probe for prostate visualization reasons. Since the sagittal scan plane field of view of a linear array is rectangular and the transaxial plane field of view is positioned to the side of the sagittal linear array, it is not possible to view the transaxial scan plane position (on edge) in the sagittal field of view. Thus, in using the biplane probe, the clinical user cannot switch from sagittal to transaxial scan planes and maintain a view of the tissue area of interest. After the transaxial scan plane is selected, the probe must be repositioned in the patient's rectum in order to visualize the tissue area of interest again. This is not only very inconvenient but drastically reduces the clinical utility of this biplane probe design.

SUMMARY OF INVENTION

A biplane ultrasound probe includes an outer casing having a longitudinal axis and support means mounted within the outer casing for supporting more than one scanning means aligned on the longitudinal axis. A plurality of scanning means are mounted on the support means along the longitudinal axis for respectively ultrasound scanning different planes of an adjacent object. Shift means shifts the support means axially within the casing independently of the casing to move either one of the scanning means into a unitary scanning position. The shift means includes actuator means for actuating the one of the scanning means shifted into the scanning position to scan a plane of the object.

FIGURES IN THE DRAWINGS

Other advantages of the present invention will be readily appreciated as the same becomes better understood by reference to the following detailed description when considered in connection with the accompanying drawings wherein:

FIG. 1 is a perspective view of the present invention;

FIG. 2 is a cross sectional view taken substantially along lines 2—2 of FIG. 1;

FIG. 3 is a side view of an assembled probe constructed in accordance with the present invention;

FIG. 4 is a side view in cross section of the present invention partially broken away wherein the inner probe is shifted within the outer casing;

FIG. 5 is a fragmentary view of one of the transducers mounted on the probe scanning a specific portion delineated on a piece of tissue through the centerline of the transducer; and FIG. 6 is a perspective view of two transducers mounted on the end of a probe having the scanned plane of the most distal transducer translated onto the scan plane of the more proximal transducer and indicating the intersection of their centerlines through the translation.

DETAILED DESCRIPTION OF THE DRAWINGS

A biplane ultrasound probe constructed in accordance with the present invention is generally shown at 10.

The probe 10 includes an outer casing generally indicated at 12 which defines a longitudinal axis of the probe 10. An inner member generally indicated at 14 provides support means mounted within the outer casing 12 for supporting a pair of ultrasound scanning transducers 16,18 aligned on the longitudinal axis of the probe 10. The transducer 16 can be a linear array or phased array for sagittal imaging and the more distal transducer 18 can be a transaxial or linear array transducer which can be a phased array or mechanical sector scanner for transaxial imaging. Each scanning transducer 16,18, respectively, ultrasound scans different orthogonal planes of an adjacent object, the object being schematically shown at 20 in FIG. 5. Alternatively, the invention can utilize transducers mounted to have parallel scan planes having focal properties or frequencies that are different.

The invention includes shift means for shifting the inner member 14 axially within the outer casing 12 independently of the outer casing 12 to move either one of the scanning transducers 16,18 into a unitary scanning position. The shift means includes actuator means for actuating one of the scanning transducers 16,18 shifted into scanning position to scan a plane of the adjacent object 20.

More specifically, each of the scanning transducers 16,18 scans a plane 23, 25 having a central ray, schematically shown at 22,24 for each transducer 16,18 respectively. The transducers 16,18 are mounted on the inner member 14 such that their central rays 22,24 are parallel relative to each other. As shown in FIG. 6, the scanning plane 25 has a central ray 24 of the scanning transducer 18 which is translated to the centerline 22 of the scanning plane 23 of the transducer 16. The central rays 22,24 are separated by a predetermined distance D. The shifting means shifts the inner member 14 a distance equal to the predetermined distance D between the central rays 22,24 to automatically position the center of each of the scanned planes 23,25 of each respective scanning transducer 16,18 on the former center of the other of the scanned planes.

More specifically, the inner member 14 includes a key 26 projecting therefrom. The key 26 projects through a slot 28 extending into the outer casing 12. The key 26 is in sliding mating relationship with the slot 28 along the longitudinal axis of the assembly 10. The key 26 provides anti-rotation means preventing relative rotation between the inner member 14 and housing 12.

Stop means engages and stops the key 26 to position either of the scanning transducers 16,18 at the scanning position. More specifically, the stop means includes a depression 31 in the key 26. The depression includes a pair of notches 30,32 extending further into the key 26 at each end of the depression 31 and spaced apart a distance D equal to the predetermined distance D between the central rays 22,24 of the scanned planes 23,25 of the respective ultrasound scanning transducers 16,18. The stop means further includes a cantilevered arm 34 mounted on a pivot 35 which pivots for selectively engaging into and releasing from either one of the notches 30,32 to lock either of the scanning transducers 16,18 in the scanning position. The assembly 10 includes biasing means schematically indicated as a spring at 36 for biasing the arm 34 on the pivot 35 to engage one of the notches 30,32 positioned thereunder. The arm 34 is exposed through a slot 38 in the outer casing 12 and is depressible against the bias of the spring 36 to pivot and disengage the arm 34 from the notch 30,32 for shifting of the inner member 14.

The actuator means of the assembly includes pressure sensitive micro-switches 40,42 mounted in each of the notches 30,32. The arm 34 engages one of the micro-switches 40,42 to actuate one of the transducers 16,18 shifted to the scanning position. This is illustrated in FIGS. 3 and 4. In FIG. 3, transducer 16 is positioned in the scanning position and the arm 34 engages the notch 30 thereby fixing the transducer 16 in the scanning position. Simultaneously, the arm 34 engages the micro-switch 40 thereby actuating the transducer 16. FIG. 4 illustrates the inner member 14 being shifted so that the notch 30 is released by the arm 34 and is in the process of being shifted for the arm 34 to engage the notch 32 and thereby contact micro-switch 42. Contact of the micro-switch 42 actuates the transducer 18 which would then be positioned in the scanning position.

The inner member 14 includes a handle portion 44 which projects from the outer casing 12 when the inner member 14 and outer casing 12 are assembled. The inner member 14 further includes a body portion 46 extending into the outer casing 12. The transducers 16,18 are mounted on the body portion 46. The shift means includes the handle portion 44 which can be manually grasped. Transducer cables 48 extend from the handle portion to a multi-wire connector on a main frame. Operating switches generally indicated at 50 can be mounted on a lower fin 52 of the outer casing 12 so that control of the probe and main frame can be accomplished by the control of a single hand on the assembly, without the necessity of operating switches on the main frame.

In operation, the arm 34 is depressed to release the notch 30,32 and the handle portion 44 is moved to or away from the outer casing to move either of the scanning transducers 16,18 into the scanning position to scan an adjacent object. The depressible portion of the arm 34 is released and one of the micro-switches is then depressed to actuate the transducer 16,18 positioned in the scanning position.

The outer casing 12 includes an opening 54, the scanning transducers 16,18 being disposed within the opening 54. The outer casing 12 includes fluid container means mounted over the opening 54 to perfect a fluid environment about the scanning transducers 16,18. More specifically, the fluid container means includes a condom 56 which is mechanically fixed to the outer casing 12 by elastic band 80 to perfect a water seal. Two O-rings 58,60 are mounted inside the outer casing 12 and about the inner member 14 to maintain a water seal so that water will not leak out of the space between the inner member 14 and the outer case 12. The outer casing 12 includes a fill tube 62 in fluid communication with the condom 56, the fill tube 62 including a portion 64 extending along the longitudinal axis of the outer casing 12. The fill tube 62 has an open end 66 adjacent the opening 54.

The present invention further provides common line indicating means for producing an image of the common lines 22,24 of the scanned planes 23,25 from each of the scanning transducers 16, 18.

Each of the scanning transducers 16,18 transmits a plurality of lines perfected as the image of an object by an individual processing system, as schematically shown in FIG. 5 at 20. In the embodiment shown, the common line between the two scan planes is the center line of each plane. The common line highlighting means can include signal generating means for transmitting an additional single line high amplitude signal in the geometric center of the plurality of lines which generate the image to highlight the centerline on the visual image processing system, indicated at 70 in FIG. 5.

Alternatively, the visual image processing system could include software for generating a highlighted line on the mainframe display which corresponds to the centerlines 22,24, depending upon which scanning transducer 16,18 is actuated.

Utilizing the invention, the centerline 22,24 of each image (sagittal and transaxial) is highlighted. As illustrated in FIG. 6, the common line shared by the planes generated by the two scanning transducers is the centerline of each plane. A portion of the tissue which is of interest is positioned on the mainframe display at the centerline of one scan plane. Translation of the transducer positions that same tissue of interest on the scan plane of the other transducer since the highlighted center line is the common line shared by the scan planes upon translation. Depending upon the orientation and positioning of the transducers, this common line may not be a centerline in either scan plane. It need only be the common line shared between the scan planes of the two transducers at the unitary position where either transducer is activated.

In use, the operator will scan the object with the first of the transducers 16,18 to perfect an image of object 20 on the image visualizing system. An image of the centerline of the image 20 will be produced, either by the generation of the high amplitude signal as discussed above or through a software package within the main frame system so as to visualize the centerline on the image visualizing system. The operator will then center a portion of the object 72, such as a suspected tumor, on the centerline image. Finally, the operator will translate the probe, as by shifting the inner probe 14, to scan with the other of the transducers 16,18 whereby the portion 72 of the object 20 is centered in the scan plane of the second mentioned transducer 16,18.

The present invention insures that the tissue of interest 72 will be centered at a point where translation of the inner probe 14 will result in the tissue of interest 72 being on the scan plane of the second operated transducer. The invention can be utilized on other intra cavity ultrasound probes such as vaginal or intraoperative probes as well as general purpose contact scan transducers.

The invention can also be useful in therapy where ultrasonic guidance of radioactive seeds are implanted to treat prostate cancer or other cancers. The probe can be used to assist the guidance of the needle implanting the seeds and monitor any migration of the seeds over time. The invention will also allow switching between two transducers to properly guide the same biopsy needle. In this environment, alignment of the needle relative to a scan can be ensured during the switching of transducers having different optical or focal characteristics thereby achieving a unitary view.

The various aspects of the present invention provide many improvements solving problems facing the designers of state of the art biplane probes. The operator utilizing the present invention can switch from one scan plane to the other without losing sight of the tissue area of interest. The electrical wiring inside the inner member 14 would be protected against moisture damage by the inner probe case perfected by the seals 58,60. For volume estimation measurements, two orthogonal images of the lesion can be rapidly obtained with the lesions centered in both images. This will enable the three major axes of the lesion to be measured and used in a volume estimation formula. For complex shape lesions, this procedure would be much more accurate than using only one image and assuming rotational symmetry of the lesion. It would also be more convenient than obtaining a set of serial scans at known intervals.

The tubes and valves associated with the filling and emptying of the condom would be part of the outer casing 12. One difficulty with present biplane probe designs is that the fill hole is on the outside of the probe and if the condom is pressed against the opening of this hole, it could be blocked preventing emptying of the condom and removal of the probe from the rectum. In the present invention, the fill hole 66 is located between the inner member 14 and outer casing 12, this orientation completely avoiding the problem of the prior art.

Most ultrasound manufacturers have designed biplane probes as retrofits to their existing equipment. Most ultrasound imagers have connectors for two transducers available. In use, the two transducers are connected to these connectors and the operator switches between the transducers with a control on the main frame for convenience. Biplane probes can easily be connected to the existing main frames because they are available to connectors for the two transducers. However, then the operator is obliged to reach over to the main frame and switch the scan planes during examination. The present invention allows the operator to select and switch between the scan planes without his hands ever leaving the probe since the shifting can be accomplished by the depression of the arm 34 and movement of the handle portion 44, as well as operation of important functions on the main frame by utilization of the switching device 50. The microswitchs 40,42 cause circuitry in the main frame to switch between transducers or connectors.

Certain manufacturers make one electrical connector on some main frames. In order to switch transducers, the operator must physically demount one transducer and mount another on this connector. This procedure is very inefficient in biplane prostate scanning and would negate the usefulness of the biplane probe. With this invention, the manufacturer need only proved a suitable box with the two electrical connectors for the biplane transducers and an output cable to the single connector on the main frame. The circuitry for switching between the transducers 16,18 would be contained in this box so that the box would electrically switch the transducers 16,18 using the control signals from the two micro-switches 40,42.

The outer casing 12 can be molded out of plastic. The buttons mounted on it can be on a small frame mounted outside of the outer casing 12 so as to protect the transducers and wiring inside the inner casing for mechanical damage due to drops and other mechanical trauma. If the outer casing 12 is damaged, it can be replaced without the expense of replacing the inner member 14. Also, the outer casing 12 can be separately sterilized in an autoclave.

If a manufacturer develops a new combination of transducers on the inner member 14, a new inner member may be inserted to the already purchased outer casing without the requirement of manufacturing or purchasing a new outer case 12.

If there is any mechanical damage or blockage to water holes 66 and tubes in the outer casing 12, then a new outer casing 12 can be substituted quite quickly and the examination continued. In the present design of prostate probes, if the water holes are damaged or blocked, then the examination must be suspended while the problem is fixed. If the problem is serious, then no more patients can be examined until the probe is repaired or replaced. The design of the present invention permits the water fill and empty function to be done by the inexpensive and replaceable outer casing 12 while retaining the useability and integrity of the inner member 14 and its two transducers 16,18.

The present invention represents a new mechanical design for biplane probes which automatically solves the problem of switching from one scan plane orientation to the other while maintaining a view of the tissue area of interest. Although the instant invention is very well suited for the examination of the prostate, the device could be used for scanning other tissues of interest.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A multiplane ultrasound probe (10) comprising: an outer casing (12) having a longitudinal axis and a unitary scanning position therein; support means (14) mounted within said outer casing (12) for supporting more than one scanning means (16,18) aligned on said longitudinal axis; a plurality of scanning means (16,18) mounted on said support means (14) along said longitudinal axis for respectively ultrasound scanning different orthogonal planes (23,25) of an adjacent object (20) when positioned at said scanning position; shifting means for shifting said support means (14) axially within said outer casing (12) independently of said scanning position of said outer casing (12) and moving either of said scanning means (16,18) into said unitary scanning position; and registry means for releasably setting any of said scanning means at said scanning position.

2. A probe as set forth in claim 1 said shifting means including actuator means for actuating the one of said scanning means (16,18) shifted into said scanning position to scan a plane of the adjacent object (20).

3. A probe as set forth in claim 2 further characterized by each of said scanning means (16,18) scanning a plane (23,25) having a common ray (22,24) intersected by the plane scanned by the other of said scanning means when positioned in said unitary position, said common rays being separated by a predetermined distance D, said shifting means translating said support means (14) a distance equal to said predetermined distance D between said central rays to automatically translate the center of each of said scan planes (23,25) on the center of the other of said scan planes.

4. A probe as set forth in claim 3 further characterized by including anti-rotation means (26) for preventing relative rotation between said support means (14) and said outer casing (12) and allowing axial movement between said support means (14) and said outer casing (12).

5. A probe as set forth in claim 4 further characterized by said anti-rotation means including a key (26) projecting from said support means (14) and a slot (28) extending into said outer casing (12), said key (26) being in sliding relationship within said slot (28) along said longitudinal axis.

6. A probe as set forth in claim 5 further characterized by including stop means for engaging and stopping said key (26) to position any one of said scanning means (16,18) at said scanning position.

7. A multiplane ultrasound probe (10) comprising: an outer casing (12) having a longitudinal axis and a unitary scanning position therein; support means (14) mounted within said outer casing (12) for supporting more than one scanning means (16,18) aligned on said longitudinal axis; a plurality of scanning means (16,18) mounted on said support means (14) along said longitudinal axis for respectively ultrasound scanning different orthogonal planes (23,25) of an adjacent object (20) when positioned at said scanning position; and characterized by shifting means for shifting said support means (14) axially within said outer casing (12) independently of said scanning position of said outer casing (12) and moving either of said scanning means (16,18) into said unitary scanning position, anti-rotation means (26) for preventing relative rotation between said support means (14) and said outer casing (12) and allowing axial movement between said support means (14) and said outer casing (12), said anti-rotation means including a key (26) projecting from said support means (14) and a slot (28) extending into said outer casing (12), said key (26) being in sliding relationship within said slot (28) along said longitudinal axis, stop means for engaging and stopping said key (26) to position any one of said scanning means (16,18) at said scanning position, said scanning means including a pair of ultrasound transducers (16,18) said stop means including a pair of notches (30,32) extending into said key (26) and spaced apart a distance D equal to said predetermined distance D between said central rays (22,24) of said scan planes (23,25), said stop means further including a cantilevered arm (34) for selectively engaging and releasing either one of said notches (30,32) to look either of said ultrasonic transducers (16,18) in said scanning position.

8. A probe as set forth in claim 7 further characterized by biasing means (36) for biasing said arm (34) to engage the one of said notches (30,32) positioned thereunder, said arm (34) being depressible to release said notch (30,32) for shifting of said support means (14).

9. A probe as set forth in claim 8 further characterized by said actuator means including a pressure sensitive micro-switch (40,42) mounted in each of said notches (30,32) on said key (26), said arm (34) engaging said one of said micro-switches (40,42) to actuate the one of said scanners (16,18) shifted to said scanning position.

10. A probe as set forth in claim 9 further characterized by said support means including an inner probe (14) slideably retained within said outer casing (12), said inner probe (14) including a handle portion (44) projecting from said outer casing (12) and a body portion (46) extending into said outer casing (12) and having said ultrasonic transducers (16,18) mounted thereon, said shifting means including said handle portion (44) for being manually grasped and said arm (34) is depressed to including an exposed depressible portion whereby said arm (34) to release said notch (30,32) and said handle portion (44) is moved to or away from said outer casing (12) to move either of said ultrasonic transducers (16,18) into said actuated position.

11. A probe as set forth in claim 1 further characterized by said outer casing (12) including an opening (54), said scanning means (16,18) being disposed within said opening (54), said outer casing (12) including fluid container means (56) mounted over said opening (54) to perfect a fluid environment about said scanning means (16,18).

12. A probe as set forth in claim 11 further characterized by said outer casing (12) including a fill tube (62) in fluid communication with said fluid container means (56), said fill tube (62) including a portion (64) extending along said longitudinal axis and having an open end (66) adjacent said opening (54).

13. A probe as set forth in claim 1 further characterized by said scanning means including a pair of transducers (16,18) mounted on said support means (14) along said longitudinal axis.

14. A probe as set forth in claim 13 further characterized by one of said transducers being a sagittal scan plane transducer (16) and the other of said transducers being a transaxial scan plane transducer (18).

15. An ultrasound probe (10) comprising: an outer casing (12) having a longitudinal axis and a unitary scanning position therein, support means (14) mounted within said outer casing (12) for supporting more than one scanning means (16,18) aligned on said longitudinal axis; a plurality of scanning means (16,18) mounted on said support means (14) along said longitudinal axis for respectively ultrasound scanning different planes (23,25) of an adjacent object (20) when positioned at said unitary scanning position; shifting means for shifting said support means (14) axially within said outer casing (12) independently of said unitary scanning position of said outer casing (12) and moving one of said scanning means (16,18) into said unitary scanning position; and registry means for setting any of said scanning means at said scanning position.

* * * * *